US012635948B2

(12) United States Patent
Cedrone et al.

(10) Patent No.: US 12,635,948 B2
(45) Date of Patent: May 26, 2026

(54) PHYSIOLOGICAL MONITORING APPARATUSES, SYSTEMS AND METHODS

(71) Applicant: The General Hospital Corporation, Boston, MA (US)

(72) Inventors: Kevin Cedrone, Somerville, MA (US); James Wright, Boston, MA (US); Kristian Olson, Holliston, MA (US); Data Santorino, Mbarara (UG); Beth Mosher, Jamaica Plain, MA (US)

(73) Assignee: The General Hospital Corporation, Boston, MA (US)

( * ) Notice: Subject to any disclaimer, the term of this patent is extended or adjusted under 35 U.S.C. 154(b) by 1439 days.

(21) Appl. No.: 16/073,245

(22) PCT Filed: Jan. 25, 2017

(86) PCT No.: PCT/US2017/014848
§ 371 (c)(1),
(2) Date: Jul. 26, 2018

(87) PCT Pub. No.: WO2017/132208
PCT Pub. Date: Aug. 3, 2017

(65) Prior Publication Data
US 2021/0204880 A1 Jul. 8, 2021

Related U.S. Application Data

(60) Provisional application No. 62/287,143, filed on Jan. 26, 2016.

(51) Int. Cl.
*A61B 5/00* (2006.01)
*A61B 5/024* (2006.01)
(Continued)

(52) U.S. Cl.
CPC .......... *A61B 5/6838* (2013.01); *A61B 5/0002* (2013.01); *A61B 5/02438* (2013.01);
(Continued)

(58) Field of Classification Search
CPC ................ A61B 5/6838; A61B 17/122; A61B 2503/045; A61B 5/02444;
(Continued)

(56) References Cited

U.S. PATENT DOCUMENTS 2,942,604 A * 6/1960 Gravlee, Jr. ..... A61B 17/12009
606/140
4,390,019 A * 6/1983 LeVeen ................ A61B 17/122
606/158
(Continued)

FOREIGN PATENT DOCUMENTS

AU 2004210661 A1 * 8/2004 .......... A61B 17/122
DE 1002005048496 A1 4/2007
(Continued)

OTHER PUBLICATIONS

Bourzac, A Health-Monitoring Sticker Powered by Your Cell Phone, MIT Tech. Rev., Aug. 3, 2016, accessed online at https://www.technologyreview.com/s/602067/a-health-monitoring-sticker-powered-by-your-cell-phone/.
(Continued)

*Primary Examiner* — Jacqueline Cheng
*Assistant Examiner* — Jonathan E. Cooper
(74) *Attorney, Agent, or Firm* — QUARLES & BRADY LLP

(57) ABSTRACT

Physiological monitoring systems, apparatuses and methods are disclosed. In an embodiment, a system includes an umbilical cord clamp having a sensor and a base station. The clamp is moveable between an open position and a clamped position in which the sensor contacts the umbilical cord to
(Continued)

sense a physiological parameter of a neonate. The base station is operable to transmit an interrogation signal wirelessly to the sensor, and in response to the interrogation signal, receive a response signal wirelessly that is indicative of the sensed physiological parameter.

29 Claims, 5 Drawing Sheets

(51) Int. Cl.
    *A61B 17/122*        (2006.01)
    *G16H 50/30*        (2018.01)

(52) U.S. Cl.
    CPC ........ *A61B 5/02444* (2013.01); *A61B 5/6823* (2013.01); *A61B 5/7203* (2013.01); *A61B 5/7275* (2013.01); *A61B 17/122* (2013.01); *G16H 50/30* (2018.01); *A61B 2503/045* (2013.01); *A61B 2560/0214* (2013.01); *A61B 2562/08* (2013.01)

(58) Field of Classification Search
    CPC ........ A61B 2017/00221; A61B 5/0002; A61B 5/02438; A61B 2562/0261; G01L 1/2293
    See application file for complete search history.

(56) References Cited

U.S. PATENT DOCUMENTS

| | | | | |
|---|---|---|---|---|
| 4,781,188 A | * | 11/1988 | Collins | A61B 17/122 |
| | | | | 606/120 |
| 4,856,517 A | * | 8/1989 | Collins | A61B 17/122 |
| | | | | 606/174 |
| 4,870,965 A | * | 10/1989 | Jahanger | A61B 17/128 |
| | | | | 606/174 |
| 5,440,295 A | * | 8/1995 | Ciecwisz | G08B 21/0288 |
| | | | | 606/120 |
| 5,575,796 A | * | 11/1996 | King | A61B 5/150038 |
| | | | | 606/120 |
| 5,584,840 A | * | 12/1996 | Ramsey | A61B 17/122 |
| | | | | 606/151 |
| 5,676,676 A | * | 10/1997 | Porter | A61B 17/122 |
| | | | | 606/151 |
| 5,713,912 A | * | 2/1998 | Porter | A61B 17/122 |
| | | | | 606/151 |
| 6,111,520 A | | 8/2000 | Allen | |
| 6,254,537 B1 | | 7/2001 | Nguyen | |
| 6,348,057 B1 | * | 2/2002 | Porat | A61B 17/122 |
| | | | | 606/120 |
| 6,425,861 B1 | | 7/2002 | Haberland | |
| 6,491,647 B1 | | 12/2002 | Bridger et al. | |
| 6,648,820 B1 | | 11/2003 | Sarel | |
| 6,855,115 B2 | | 2/2005 | Fonseca | |
| 7,147,604 B1 | | 12/2006 | Allen | |
| 7,245,117 B1 | | 7/2007 | Joy | |
| 8,727,980 B2 | | 5/2014 | Coelho | |
| 8,892,181 B2 | | 11/2014 | Wolfberg | |
| 8,971,936 B2 | | 3/2015 | Derchak | |
| 9,002,427 B2 | | 4/2015 | Tupin, Jr. | |
| 9,282,893 B2 | | 3/2016 | Longinotti-Buitoni | |
| 2001/0035824 A1 | | 11/2001 | Fourie et al. | |
| 2002/0140559 A1 | * | 10/2002 | Zhou | A61B 5/681 |
| | | | | 340/988 |
| 2003/0074009 A1 | * | 4/2003 | Ramsey | A61B 17/122 |
| | | | | 606/120 |
| 2003/0120286 A1 | | 6/2003 | Burbank | |
| 2006/0283007 A1 | | 12/2006 | Cros | |
| 2006/0287602 A1 | | 12/2006 | O'Brien | |
| 2007/0100215 A1 | | 5/2007 | Powers | |
| 2007/0199385 A1 | | 8/2007 | O'Brien | |
| 2007/0276273 A1 | * | 11/2007 | Watson, Jr. | A61B 5/282 |
| | | | | 600/391 |
| 2009/0030318 A1 | | 1/2009 | Lemke et al. | |
| 2009/0203972 A1 | | 8/2009 | Heneghan | |
| 2010/0016685 A1 | * | 1/2010 | Muehlsteff | A61B 5/113 |
| | | | | 600/595 |
| 2010/0109875 A1 | | 5/2010 | Ayon | |
| 2010/0245091 A1 | | 9/2010 | Singh et al. | |
| 2012/0095531 A1 | | 4/2012 | Derbas et al. | |
| 2012/0146796 A1 | | 6/2012 | Margon | |
| 2012/0203081 A1 | | 8/2012 | LeBoeuf | |
| 2012/0232357 A1 | * | 9/2012 | Coelho | A61B 5/72 |
| | | | | 600/301 |
| 2013/0109931 A1 | | 5/2013 | Ng | |
| 2014/0276148 A1 | * | 9/2014 | Kim | A61B 5/746 |
| | | | | 600/502 |
| 2014/0288551 A1 | | 9/2014 | Bharmi | |
| 2015/0142008 A1 | * | 5/2015 | Hsiao | A61B 17/12009 |
| | | | | 606/120 |
| 2016/0172578 A1 | * | 6/2016 | Valbin | H01L 41/0533 |
| | | | | 600/300 |
| 2016/0287103 A1 | * | 10/2016 | Saponas | A61B 5/6824 |
| 2017/0007257 A1 | * | 1/2017 | Potter | A61B 17/122 |

FOREIGN PATENT DOCUMENTS

| | | | | |
|---|---|---|---|---|
| KR | 101341063 B1 | * | 12/2013 | A61M 1/00 |
| WO | 1999065004 | | 12/1999 | |
| WO | 2001035837 A1 | | 5/2001 | |
| WO | WO 2008076464 A2 | | 6/2008 | |
| WO | 2012021900 A1 | | 2/2012 | |
| WO | WO-2013063144 A1 | * | 5/2013 | A61B 5/02444 |

OTHER PUBLICATIONS

CardioMEMS Champion™ Heart Failure Monitoring System, Circulatory System Devices Advisory Panel, FDA, PMA P100045, IDE G060187, Dec. 2011, http://www.fda.gov/ucm/groups/fdagov-public/@fdagov-afda-adcom/documents/document/ucm284021.pdf.

Dawson JA, et al. Comparison of heart rate and oxygen saturation measurements from Masimo and Nellcor pulse oximeters in newly born term infants. Acta Paediatr. 2013;102(10):955-60.

Ersdal H. When early and often counts. Pract Midwife. 2015;18(8):9-11.

Ersdal HL, et al. Early initiation of basic resuscitation interventions including face mask ventilation may reduce birth asphyxia related mortality in low-income countries: a prospective descriptive observational study. Resuscitation. 2012;83(7):869-73.

Ersdal HL, et al. Timing of cord clamping in relation to start of breathing or ventilation among depressed neonates—an observational study. Bjog. 2015;24(10):1471-0528.

European Patent Office, Supplementary Partial European Search Report for application EP17744807, mailed on Jul. 31, 2019, 13 pages.

FDA, Cardiac Monitor Guidance (including Cardiotachometer and Rate Alarm), FDA CDRH, Nov. 5, 1998, http://www.ida.gov/downloads/MedicalDevices/DeviceRegulationandGuidance/GuidanceDocuments/ucm073941.pdf.

FDA, CardioMEMS HF System P100045, FDA Approval, May 28, 2014, http://www.fda.gov/MedicalDevices/ProductsandMedicalProcedures/DeviceApprovalsandClearances/Recently-ApprovedDevices/ucm400550.htm.

Kamlin CO, et al. Accuracy of clinical assessment of infant heart rate in the delivery room. Resuscitation. 2006;71 (3):319-21.

Katheria A, et al. Electrocardiogram provides a continuous heart rate faster than oximetry during neonatal resuscitation. Pediatrics. 2012;130(5):2012-0784.

Kattwinkel J, et al. Part 15: neonatal resuscitation: 2010 American Heart Association Guidelines for Cardiopulmonary Resuscitation and Emergency Cardiovascular Care. Circulation. 2010; 122(18 Suppl 3):971119.

Lawn JE, et al. 4 million neonatal deaths: when? Where? Why? Lancet. 2005;365(9462):891-900.

(56)  References Cited

OTHER PUBLICATIONS

Msemo G, et al. Newborn mortality and fresh stillbirth rates in Tanzania after helping babies breathe training. Pediatrics. 2013;131(2):2012-1795.

Van Vonderen JJ, et al. Pulse oximetry measures a lower heart rate at birth compared with electrocardiography. J Pediatr. 2015;166(1):49-53.

Wyckoff MH, et al. Part 13: Neonatal Resuscitation: 2015 American Heart Association Guidelines Update for Cardiopulmonary Resuscitation and Emergency Cardiovascular Care (Reprint). Pediatrics. 2015;136(2):14.

European Patent Office, Extended European Search Report and search opinion for application 17744807.3, dated Dec. 20, 2019, 12 pages.

International Search Report and Written Opinion for international application No. PCT/US2017/014848 dated May 23, 2017, 15 pages.

* cited by examiner

PHYSIOLOGICAL MONITORING APPARATUSES, SYSTEMS AND METHODS

CROSS REFERENCE TO RELATED APPLICATIONS

This application is a U.S. National Phase of PCT Application No. PCT/US17/14848 filed on Jan. 25, 2017, which claims priority to U.S. provisional application No. 62/287,143, filed Jan. 26, 2016, the entire contents of which are incorporated herein by reference.

STATEMENT REGARDING FEDERALLY SPONSORED RESEARCH

Not Applicable.

BACKGROUND OF THE DISCLOSURE

The present disclosure relates generally to physiological monitoring systems, apparatuses and methods. More specifically, the present disclosure relates to neonatal physiological monitoring systems, apparatuses and methods.

Every year, an estimated 6-10 million newborns require assistance to take their first breath. Early initiation of ventilation soon after birth is crucial for newborn neurological outcomes and survival. This survival is optimized if effective newborn ventilation is initiated within the first 60 seconds after birth. If a newborn has low birth weight, is born pre-term, has poor muscle tone, or has bluish skin (cyanosis), the newborn is more likely to require assistance to begin breathing. In some cases, simple warming and stimulation is enough. But for millions of newborns, a health provider is required to initiate mechanical ventilation with a resuscitation Bag-Valve-Mask device in a timely manner. Time is of the essence because every 30 seconds delay to initiation of ventilation after birth increases the risk of death by 16%.

Despite the time sensitive nature within which effective resuscitation needs to be initiated for any baby after birth, essential requisite actions are needed before ventilation. At minimum, a non-breathing baby needs to be dried thoroughly, stimulated, and separated from the mother. Maternal separation is required in most situations because effective ventilation requires a firm surface onto which the non-breathing baby must be placed. These processes, if not done in a quick and efficient way, delay the time to initiation of ventilation.

Improvement in heart rate is the first physiological response to effective ventilation. Currently, the Neonatal Resuscitation Program ("NRP") recommends electrocardiogram ("ECG") monitoring during resuscitation for reliable heart rate monitoring. However, establishment of ECG monitoring in this situation is time consuming, and requires additional human resources often lacking in most developing countries due to cost barriers in LMIC. In addition, the attachment of ECG leads to the newborn is problematic due to vernix and or amniotic fluid. Although manual umbilical cord pulse palpation or auscultation with a stethoscope are alternatives, these alternatives result in excessive interruption of ventilation and are unreliable.

SUMMARY

In an embodiment, a neonate physiological monitoring system includes an umbilical cord clamp and a base station operable with the clamp. The umbilical cord clamp includes a sensor and the clamp moves between an open position and a clamped position in which the sensor contacts the umbilical cord to sense a physiological parameter of a neonate. The base station is configured to transmit an interrogation signal wirelessly to the sensor, and in response to the wirelessly transmitted interrogation signal, receive a response signal wirelessly that is indicative of the sensed physiological parameter of the neonate.

In another embodiment, a neonate physiological monitoring method includes sensing a physiological parameter of a neonate via a sensor coupled to an umbilical cord of the neonate, transmitting an interrogation signal wirelessly to the sensor, and in response to transmitting the interrogation signal, receive a response signal wirelessly that is indicative of the sensed physiological parameter of the neonate.

In yet another embodiment, an umbilical cord clamp includes first and second clamping arms and a sensor coupled to the second arm. The first and second arms move relative to each other between a first clamped position in which the sensor contacts the umbilical cord to sense a physiological parameter of a neonate and the clamp does not occlude blood flow in the umbilical cord, and a second, different clamped position in which the sensor contacts the umbilical cord to sense the physiological parameter of the neonate and the clamp occludes blood flow in the umbilical cord.

DETAILED DESCRIPTION

The physiological monitoring apparatuses, systems and methods of the present disclosure can help reduce the time to ventilation, reduce ventilation interruptions, prioritize essential ventilation, and provide birth attendants with a more objective assessment of the condition of a neonate or newborn, which positively impacts resuscitation outcomes. The apparatuses, systems and methods can also be used with patients of other ages and for a variety of parameters to aid in rapid assessments.

Figure 1:
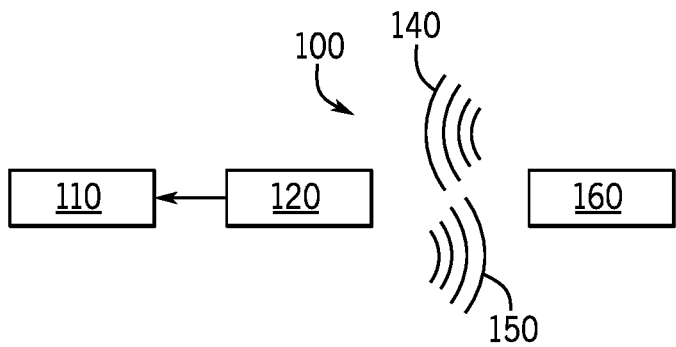
FIG. 1 is a schematic diagram illustrating an embodiment of a physiological monitoring system of the present disclosure.

FIG. 1 is a schematic diagram illustrating a non-limiting embodiment of a physiological monitoring system 100 of the present disclosure in which the speed and quality of physiological monitoring in a neonatal resuscitation setting is improved. It should be appreciated that physiological monitoring system 100 is not limited to newborns and could be used in other clinical settings for patients of different ages. System 100 generally includes one or more sensing units 120 (e.g., an umbilical cord clamp having a sensor), and a base station 160 (e.g., a neonatal bed or platform having electronics including processing circuitry). Sensing unit 120 is configured to measure or sense a physiological parameter of a patient or neonate 110 (e.g., a mechanical pulsation of the umbilical cord that results from the neonate's heart beat). Sensing unit 120 does not have to rely upon active electronic signaling, or electrical wiring between sensing unit 120 and base station 160. Base station 160 can instead actively interrogate sensing unit 120 by sending or transmitting a wireless signal 140 to sensing unit 120, which elicits or produces a response signal 150 indicative of the sensed physiological parameter of the neonate 110. Base station 160 can be configured to process or interpret the response signal 150 to determine a property or information regarding the physiological parameter (e.g., a heart rate, a heartbeat strength, a trend in the heartrate) sensed by the sensing unit 120 and provide alarms, alerts or notifications such as a notification to a neonatal nurse or other attendant clinician.

Figure 2:
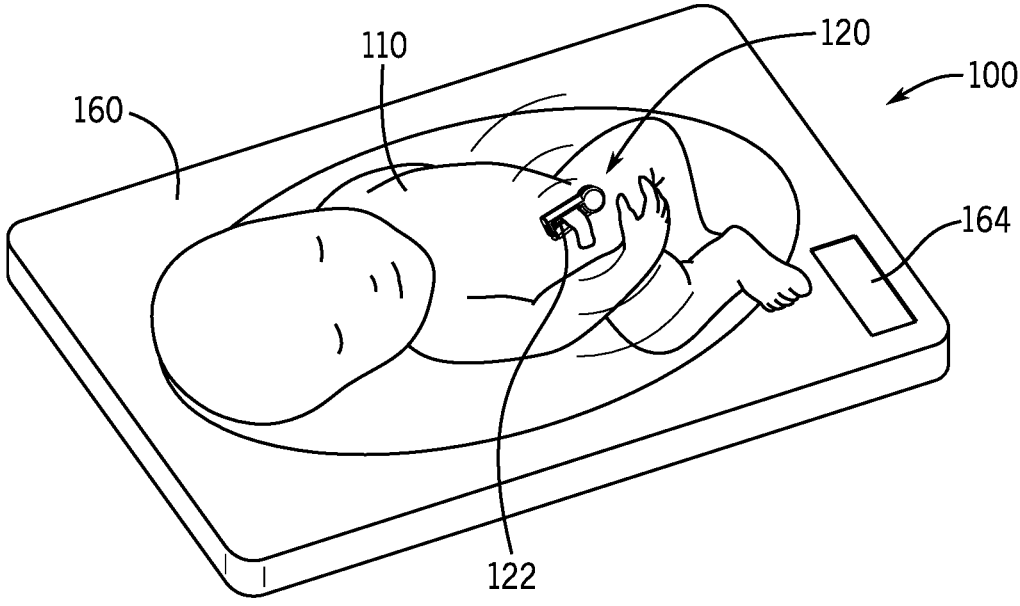
FIG. 2 illustrates an example of the physiological monitoring system of FIG. 1 having an umbilical cord sensing unit for use in a newborn care setting.

FIG. 2 illustrates a non-limiting example of the physiological monitoring system 100 of FIG. 1 in which the sensing unit 120 is in the form of an umbilical cord sensing unit or clamp having a sensor 122. Sensing unit 120 and sensor 122 are coupled to a neonate 110. Neonate 110 is lying upon a surface of base station 160, which is in the form of a bed or platform. Base station 160 includes electronic or processing circuitry (discussed below) and optionally a display 162, which can provide audio, visual and/or tactile feedback information relating to the sensed physiological parameter of the neonate. Sensor 122 can be coupled to, attached or otherwise embedded in clamp 120. When clamp 120 is coupled to the umbilical cord of neonate 110, sensor 122 senses or detects a physiological parameter of the neonate 110. In an embodiment, the physiological parameter sensed by the sensor 122 is a mechanical pulsation of the neonate's umbilical cord, which can be useful in quickly and accurately determining a neonate's heart rate immediately after birth. Sensor 122 is interrogated remotely or wirelessly by base station 160, and the sensed physiological parameter of neonate 110 can be communicated to base station 160 wirelessly. Base station 120 processes or interprets the communicated signal, and determines a property or information related to the physiological parameter of the neonate 110 (e.g., the heart rate value, heart beat strength, or trend in the heart rate), so that useful feedback can be provided to a user of the system. For example, a clinician can be fed with information as to whether the neonate's heart rate has fallen below or risen above certain thresholds, which can indicate adequate or inadequate neonatal breathing or resuscitation and be utilized in determining whether the neonate's condition is stable, improving or degrading.

Figure 3:
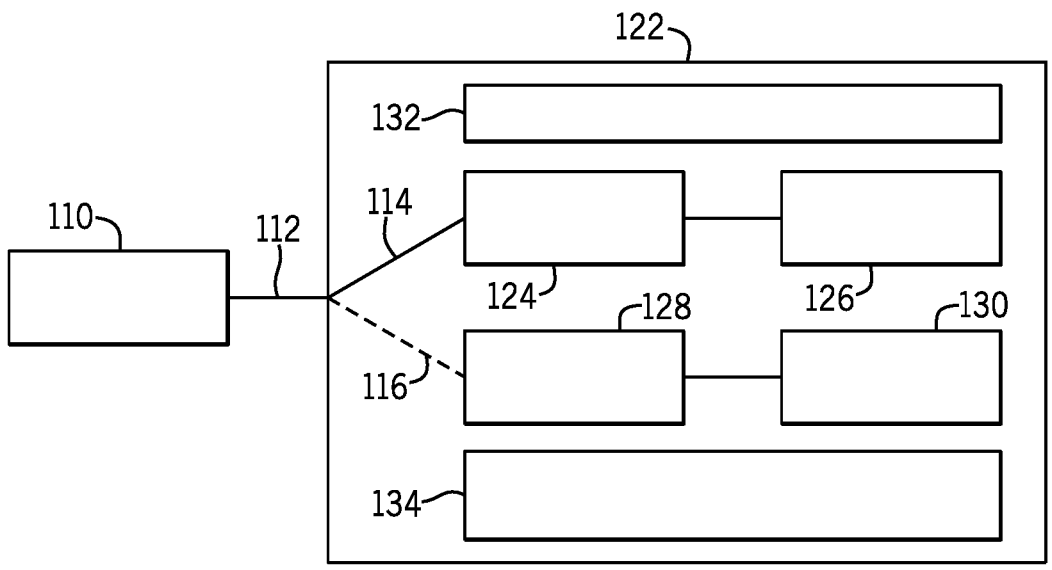
FIG. 3 is a schematic diagram illustrating an embodiment of a sensor for use with any of the physiological monitoring apparatuses, systems and methods of the present disclosure.

FIG. 3 is a schematic diagram illustrating a non-limiting embodiment of various components of sensor 122 for use with any of physiological monitoring systems apparatuses or methods of the present disclosure. Each of the components of sensor 122 can be located on a printed circuit board (e.g., a flexible circuit) or any other suitable electronics platform. Sensor 122 is embedded or otherwise coupled to sensing unit 120, and is physically coupled to the umbilical cord or stump 110 of a neonate, as illustrated by solid line 112. Sensor 122 includes one or more measurement transducer 124, one or more reference transducer 128, and electrical circuits 126, 130, 132, and 134.

Transducer 124 is physically coupled to or contacts (i.e., mechanically) the umbilical cord or stump 110 of neonate, and is responsive to a physiological parameter of the umbilical cord 110, as illustrated by solid line 114. That is, transducer 124 senses or measures the mechanical action or pulsation of umbilical cord 124 by changing its electrical properties relative to some baseline properties. In one embodiment, transducer 124 is an electrical capacitor in which mechanical or physical pulsations from umbilical cord 110 alter the capacitance of the capacitor. Transducer 124 operates or communicates with electrical circuit 126, which captures or senses changes in the electrical properties of transducer 124. Electrical circuit 126 can include one or more radio frequency antenna having a baseline or resonant frequency that changes in response to the changes in the electrical properties of transducer 124.

Unlike measurement transducer 124, reference transducer 128, does not respond or react to the physiological parameters resulting from the pulsations of umbilical cord 110, as illustrated by the dashed line 116. Reference transducer 128 can be an electrical capacitor in which mechanical or physical pulsations that are not from umbilical cord 110 alter the capacitor's capacitance (e.g., increases or decreases nominal value or frequency response). Reference transducer 128 operates or communicates with electrical circuit 130, which captures or senses changes in the electrical properties of transducer 128 that do not result from the umbilical cord pulsations. Thus, any change in the electrical properties sensed by electrical circuit 130 can be attributed to background noise or interference rather than pulsations from the umbilical cord of the neonate. The background noise or interference can be isolated, cancelled or removed from the response of the measurement transducer 124 and its electrical circuit 126, so that the information regarding the physiological parameter or the property of the physiological parameter can be determined more accurately. Electrical circuit 130 can include one or more radio frequency antenna having a baseline or resonant frequency that changes in response to the changes in the electrical properties of transducer 128 that do not result from umbilical cord pulsations.

Electrical circuit 132 includes one or more electrical components that can receive power wirelessly (e.g., from base station 160) to power one or more of the components of sensor 120. In one example, electrical circuit 132 includes at least one power receiving antenna to receive power wirelessly from base station 160 via induction, and an element to store the received power (e.g., a battery). One or more of the components of sensor 120 can be powered by the received or stored power. Circuit 132 can also include at least one antenna that is tuned to the frequency of base station 160.

Electrical circuit 134 includes one or more electrical components that can be electrically excited by base station 160 to produce an identifier. In an embodiment, the base station 160 can excite or power the electrical circuit 134 to produce a pre-programmed identifier (e.g., via standard RFID/NFC technology). The identifier can be used by the base station 160 to, for example, provide at least one of calibration instructions, a unique reference identifier (e.g., for identifying data records of a newborn or identifying the newborn itself), or alarm response thresholds or alert notifications. One such example of an alarm or alert can be an indication that a clinician should consider whether a particular sensor or clamp may be more suitable for a particular neonate based upon that neonate's birthweight or other risk factors.

Figure 4:
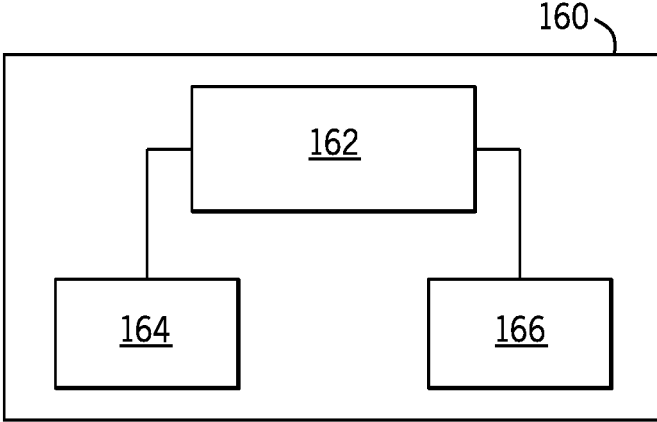
FIG. 4 is a schematic diagram illustrating an embodiment of a base station for use with any of the physiological monitoring apparatuses, systems or methods of the present disclosure.

Turning to FIG. 4, FIG. 4 is a schematic diagram illustrating a non-limiting embodiment of a base station 160 for use with any of the physiological monitoring apparatuses, systems or methods of the present disclosure. In general, base station 160 operates to transmit a signal to sensor 122 of sensing unit 120, and in response to the transmitted signal, receive a response signal that is indicative of a physiological parameter sensed by the sensing unit 120. Base station 160 can process or interpret the response signal and determine information about the signal. The processed or determined information can be stored for record tracking, retrieving or transmitting that information at a later time. In an embodiment, the base station 160 provides health information to a user of the system (e.g., a heart rate, a heart rate trend or an alarm) in the form of a tactile, audio and/or visual feedback. In certain embodiments, base station 160 includes a display 166 for providing the information to a user, and can be configured to transmit an excitation or power signal to sensor 120.

More specifically and referring to the components illustrated in the embodiment of FIG. 4, base station 160 includes at least one controller 162, at least one transceiver 164, and optionally at least one display 166. As noted above, base station 160 can be implemented as a bed or platform upon which a neonate lies so that the sensing unit or clamp 120 can be quickly coupled to a neonate lying on the bed and the adequacy of the neonate's resuscitation or breathing can be determined quickly after birth. The bed or platform can comprise a durable, surface-sterilized structure that is sized and shaped for a newborn to lie upon the surface, and to be hung in place when not in use. In alternative embodiments, base station 160 can be implemented in different forms, such as a hospital bed for patients of different ages or part of a wall or other suitable structure within a healthcare facility. Transceiver 164 can include one or more wireless antenna for redundancy, or for communication with different types of sensors, transducers or antenna of sensing unit 120. Each antenna of transceiver 164 can be installed or arranged to detect or sense signals from sensor unit 120 at different ranges of distances or orientations. At least one of the antenna of sensor 120 can be tuned to the frequency of one or more of the antenna of base station 160. In an embodiment, transceiver 164 is configured to transmit a signal to the sensor 122 of sensing unit 120, and in response to the transmitted signal, receive a response signal that is indicative of a physiological parameter sensed by the sensing unit 120. Display 166 can be any suitable display device for providing information to a user, such as heart rate, heart strength, or a heartbeat trend. In certain embodiments, display 166 includes at least one or more of a visual, audio, or tactile feedback components (e.g., one or more of a monitor, speaker, or vibrating components).

Controller 162 includes at least one processor and at least one memory device storing a plurality of instructions, which when executed by the at least one processor causes the system to perform various functions of the physiological monitoring systems and methods of the present disclosure. Controller 162 can generally operate to transmit a signal(s) from the transceiver 164 to the sensing unit 120, and in response to the transmitted signal(s), receive a response signal(s) indicative of the physiological parameter of a patient or neonate. Controller 162 can process or interpret the signal(s) to determine information regarding the physiological parameter and provide information to a clinician based upon the response signal (e.g., provide an indication of a patient's heartbeat, heart strength or a trend in the heart rate). Base station 160 can also be configured to operate with a central processing computer or work station, such as a central nursing station or monitor.

Mechanical or physical pulsations of an umbilical cord can be considered non-peripheral pulses when compared to sensing via hand or foot-mounted pulse oximeters, for example. As such, umbilical cord pulsation signals can be stronger and more reliable indicators of a neonate's heart rate or heartbeat, requiring less amplification and having less susceptibility to noise or interference. But accurate monitoring of physiological parameters of a neonate can be challenging because the newborn's heartrate can be weak, rapidly changing, or obfuscated by other phenomena (e.g., myoelectric signals relating to respiration, physical motion of chest and abdomen associated with ventilation, and other radiofrequency transmissions or sounds within the vicinity of the newborn). The controller 162 of base station 160 can therefore be configured or programmed to isolate the intermittent phenomenon of the physiological parameter being sensed from confounding sources of spurious signal or noise. In one embodiment, controller 162 is configured to utilize a Goertzel algorithm to isolate the physiological parameter of the neonate. The controller 162 can be configured to utilize the algorithm to measure or determine the frequency of the response signal(s) from sensor unit 120 to test at least one of a presence, absence or a strength of the response signal. The presence of an expected reference signal can indicate that sensor 120 is not activated or stimulated (e.g., not stimulated by a heartbeat), while the absence of an expected reference signal can indicate that sensor 120 is activated or stimulated (e.g., activated by a heartbeat). For example, a steady electrical signal can be disrupted due to a heartbeat. The steady reference signal can signify that the clamp or sensing unit 124 is within range, and a heartbeat can interrupt or disrupt that steady signal. Controller 162 can be configured to apply the algorithm to test individual frequency components, rather than to test a continuous spectrum of frequencies like a fast Fourier transform ("FFT"). The individual tested frequencies can be selected to match the frequency of measurement transducer 124 and reference transducer 128. By utilizing the algorithm and focusing on individual frequencies and using pre-computed and only real (i.e., non-complex) terms, the present disclosure provides a computationally efficient algorithm, allowing the systems, apparatuses and methods of the present disclosure to operate with an inexpensive controller or processor, making the systems, apparatuses and methods more accessible in resource-limited settings.

Controller 162 can be configured to compare several adjacent frequencies to quantify the magnitude of a frequency shift of signals from sensor unit 120. The magnitude of frequency shifts relate to the magnitude of mechanical disturbance, which is in turn related to the strength of the umbilical pulsation or physiological parameter being sensed. Controller 162 can determine a pulsation strength, rate and/or trend, which can be useful indicators of the success of ventilation efforts on a neonate.

In an embodiment, controller 162 is configured to process and isolate or cancel noise and interference signals by comparing noise or interference signals received from measurement transducer 124 to the signals received from reference transducer 128. That is, reference transducer 128 can be configured such that its response signal(s) do not change based upon umbilical cord pulsation, as discussed above. Thus, any deviation from an expected reference response can be used as an indication of spurious signals and/or background noise. Controller 162 can be configured to compensate for such spurious signals or background noise by comparing the response of measurement transducer 124 to the response of reference transducer 128.

Figure 5:
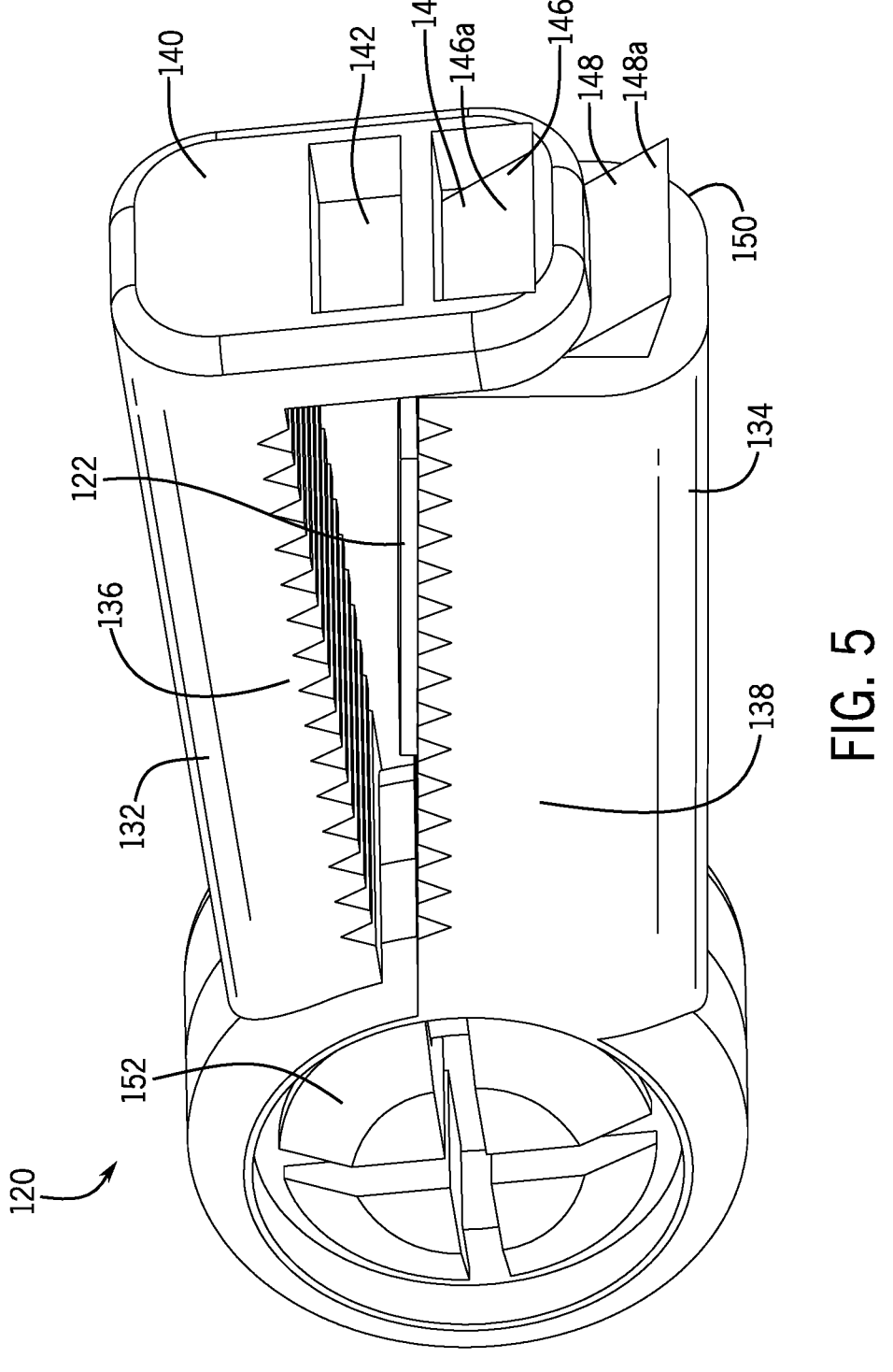
FIG. 5 illustrates an embodiment of a sensing unit or clamp for use with any of the physiological monitoring systems or methods of the present disclosure.

FIG. 5 illustrates a non-limiting embodiment of a sensing unit 120 in the form of a clamp for use with any of the physiological monitoring systems or methods of the present disclosure. Clamp 120 is structured and arranged to be clamped or attached to an umbilical cord or stump of a neonate, and generally includes a first clamping arm 132, a second clamping arm 134 and a sensor 122. Clamping arms 132, 134 can comprise any material suitable for use with a neonate or other patient, and can be manufactured separately for simplicity and cost-effectiveness. In certain embodiments, clamping arms 132, 134 comprise a polycarbonate or polyethylene material. Sensor 122 can be configured in accordance with the description of sensor 122 described in connection with FIG. 3 and can be fixedly or moveably (e.g., resiliently) coupled to either one of the clamping arms 132, 134 via a resilient coupling mechanism (discussed below). The resilient coupling of sensor 122 to either one of the arms 134, 136 allows the sensor 122 to move between (i) a first non-compressed or non-deformed position in which the clamp 120 maintains mechanical contact with the umbilical cord to sense the physical pulsation of the cord without excessive pressure (e.g., without the clamp occluding blood flow in the cord), and (ii) a second, compressed or deformed position in which the clamp 120 contacts the umbilical cord to sense the physiological parameter of the cord and applies a pressure to the cord that is greater than the pressure applied in the first position (e.g., a pressure sufficient to occlude or arrest blood flow in the cord). Thus, clamp 120 can be used in two different modes, one mode in which the clamp 120 senses the physiological parameter of the neonate without occluding blood flow, and another mode in which the clamp 120 senses the physiological parameter of the neonate and occludes blood flow (e.g., hemostasis). The resilient coupling of the sensor 122 to the clamp 120 also allows the clamp to be used with a variety of differently sized umbilical cords, making the clamp more versatile.

First clamping arm 132 includes a plurality of teeth 136 and a lip 140. Teeth 136 extend from an inner surface of arm 132, and lip 140 extends from an end portion of the arm 132, generally perpendicular to the body of arm 132. Lip 140 includes first 142 and second 144 notches defined therein. Like first arm 132, second clamping arm 134 includes a plurality of teeth 138 extending from an inner surface of arm 134. Teeth 136 of first clamping arm 132 and teeth 138 of the second clamping arm 134 each provide better gripping action for the clamp 120 (e.g., when attaching the clamp 120 to a wet or slippery umbilical cord immediate after a neonate is born). Second clamping arm 134 further includes first 146 and second 148 protrusions extending outwardly from an end face 150 of arm 134.

The first clamping arm 132 is moveable relative to the second clamping arm 134 via a pivot or hinge mechanism 152. Stops, detents or any other suitable features can operate with pivot mechanism 152 to provide simplified mechanical movement between the open and clamped positions of arms 132, 134, and to provide feedback to a user regarding the position of the arms 132, 134 (e.g., between open and clamped positions). It should be appreciated that any other suitable hinge or pivot configurations can be utilized to allow first clamping arm 132 to move relative to the second clamping arm 134 between open and clamped positions. In certain embodiments, arms 132, 134 are coupled directly to each other or are integral with one another (e.g., made of a single piece). In one example, the relative movement between arms 132, 134 occurs via a living hinge mechanism.

Figure 6:
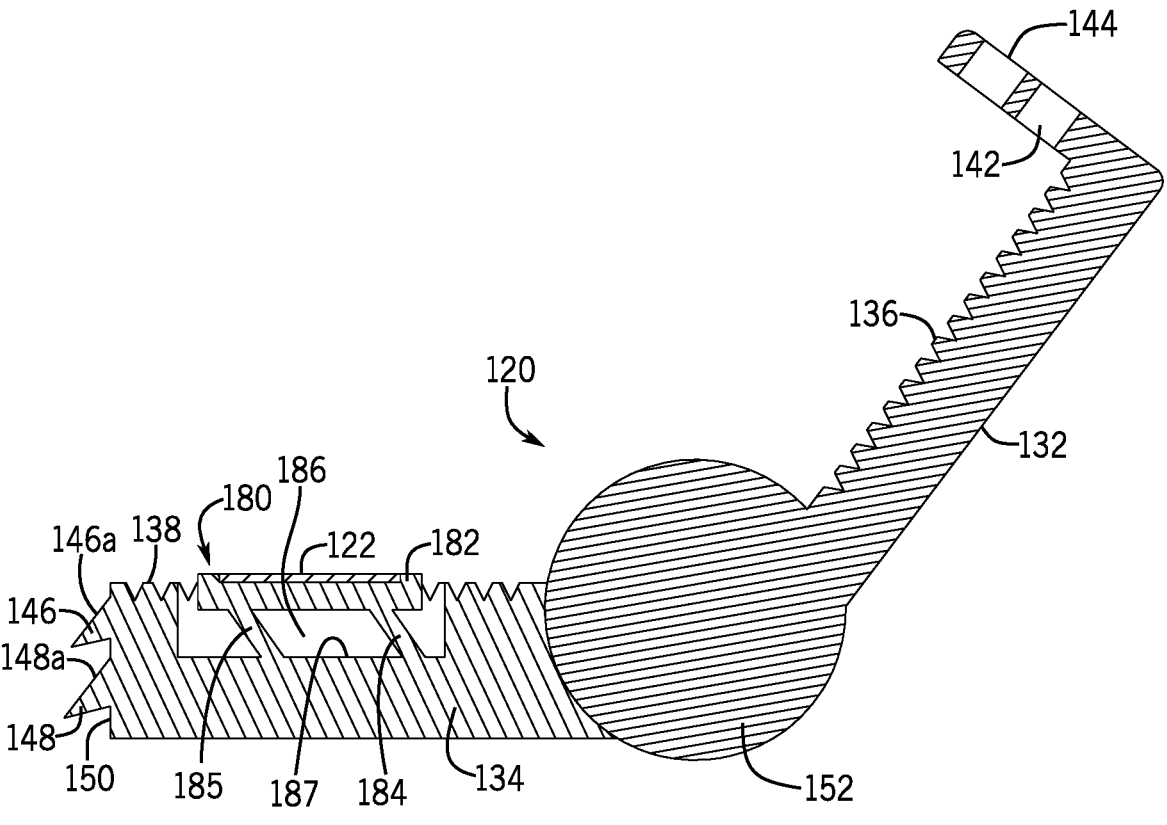
FIG. 6 is a cross-sectional view of the clamp of FIG. 5 showing the clamp in an open or non-clamped position.
Figure 7:
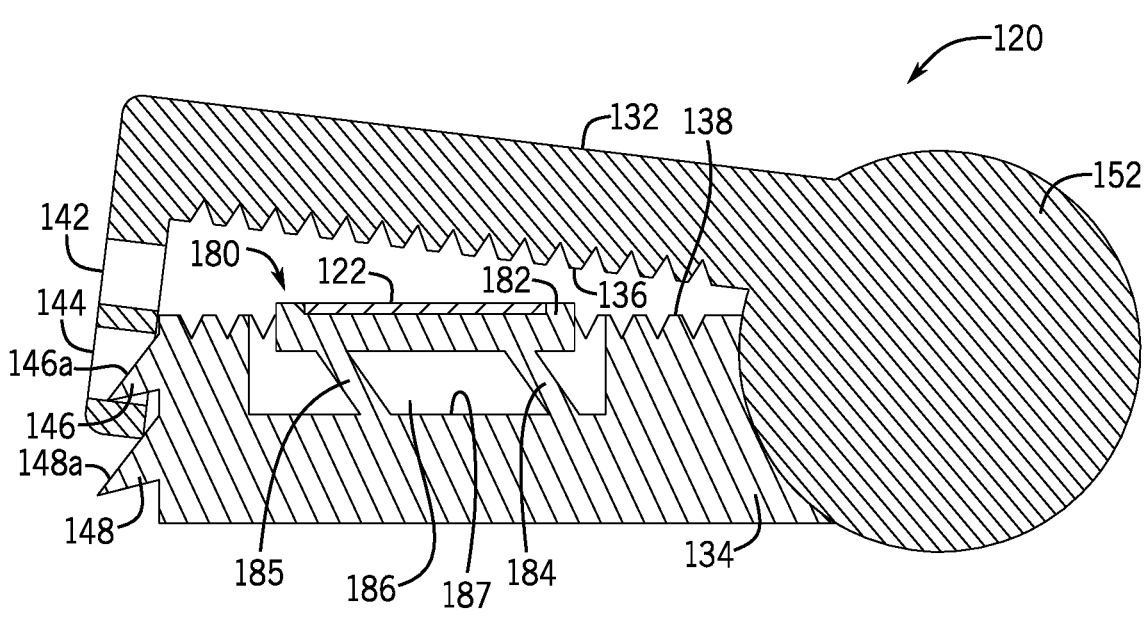
FIG. 7 is a cross-sectional view of the clamp of FIG. 5 showing the clamp in a clamped position.
Figure 8:
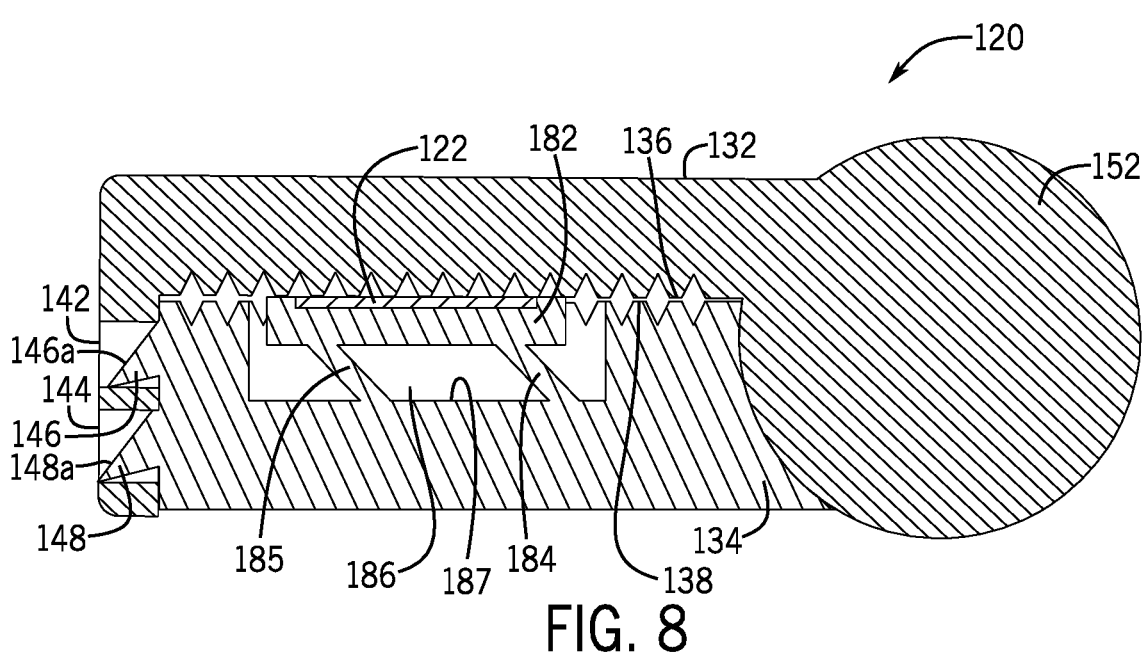
FIG. 8 is a cross-sectional view of the clamp of FIG. 5 showing the clamp in another clamped position.

FIGS. 6, 7 and 8 are cross-sectional views of the clamp 120 of FIG. 5 illustrating clamp 120 in an open or non-clamped position (FIG. 6) and in two different clamped positions (FIGS. 7 and 8). The clamps 120 illustrated in FIGS. 6, 7 and 8 show the same components described above in connection with FIG. 5. Those components in FIGS. 6, 7 and 8 are marked with the same element numbers as used in FIG. 5. The description of those elements including each of the alternatives discussed above in connection with FIG. 5 apply to like element numbers in FIGS. 6, 7 and 8. FIGS. 6, 7 and 8 additionally illustrate a resilient coupling mechanism 180 that resiliently couples sensor 122 to clamping arm 134. It should be appreciated that sensor 122 need not be movably or resiliently coupled to clamp 120 in some embodiments, and can instead be fixedly coupled to, integrated with or otherwise embedded within unit 120.

Resilient coupling mechanism 180 is in the form of a deformable cantilever like structure in which a compliant or resilient material (e.g., the material of arms 184, 185) is able to deform when a force is applied to it, allowing the sensor 120 to move within a cutout 186 defined in the second arm 134. The compliant material can be made of the same or different material as the arms 132, 134. In particular, mechanism 180 includes compliant or deformable legs 184, 185, and a board or plate 182 onto which sensor 122 is coupled, attached or embedded. Legs 184, 185 extend from plate 182 to a base wall 187 of the cutout 186 defined in arm 134. Legs 184, 185 in some embodiments are dimensioned and/or angled with respect to the base wall 187 so that (i) upon application of a force to the plate 182, legs 184, 185 compress or deform, causing the plate 182 and sensor 122 (or just the sensor 122 if no plate) to move within cutout 186 towards base wall 187, and (ii) upon release of the force, legs 184, 185 return to the non-deformed or non-compressed state, causing the plate 182 (or just the sensor 122 if no plate) to move within cutout 186 away from base wall 187. The sensor 122 (or the plate 182 holding the sensor 122) can move a few millimeters within the cutout (e.g., 1 or 2 millimeters) in certain embodiments. In one embodiment, the legs 184, 185 are dimensioned to be thinner at the base of the legs (i.e., towards the base wall 187) and thicker near the plate 182 to provide at least part of the resilient or deformable bending action of the legs 184, 185. The legs 184, 185 can be angled at less than 90 degrees (e.g., around 45 degrees) with respect to the base wall 187 in certain embodiments. It should be appreciated that the resilient coupling mechanism 180 can be any physical constructions that allows the plate 182 and sensor 122 (or just the sensor 122 by itself without the plate 182) to move towards the base wall 187 via a force acting upon the plate 182 and sensor 122 (e.g., a compression force), and to spring back or return to the initial position of the plate 182 and sensor 122 upon release of that force. In one embodiment, legs 184, 185 can be compressible springs. In other embodiments, legs 184, 185 can be a single deformable structure such as a single spring or a single compliant arm having a desired thickness and/or angle with respect to the base wall.

Referring more specifically to the operation of clamp 120 and the resilient coupling of sensor 122 to arm 134, a user attaches clamp 122 to a neonate's umbilical cord by moving arms 132, 134 from an open or non-clamping first position (e.g., FIG. 6), to one of the clamped positions (e.g., FIGS. 7 and 8). To move the arms 132, 134 from the open position to the clamped position illustrated at FIG. 7, a user moves first arm 134 about a pivot or hinge via mechanism 152, such that notch 144 slides past or over the ramp 146a and protrusion 146 locates within notch 144. When protrusion 146 is located within the notch 144 as illustrated in FIG. 7, the clamp 120 is in a clamped position in which sensor 122 has not been moved relative to arm 134 and clamp 120 is held in contact with the umbilical cord so that sensor 120 can sense the neonate's physiological parameter without the clamp occluding blood flow in the cord. To move the clamp 120 from the open position of FIG. 6 to the clamped position of FIG. 8, or from the clamped position of FIG. 7 to the clamped position of FIG. 8, a user moves first arm 134 about the hinge or pivot via mechanism 152 so that notches 142, 144 slide past or over the ramps 146a, 148a and protrusions 146, 148 locate within notches 142, 144, respectively. When protrusions 146, 148 are located within the respective notches 142, 144, clamp 120 is in a clamped position in which the sensor 122 has been moved relative to arm 134 (e.g., within the cutout 186) and clamp 120 is held in contact with the umbilical cord so that sensor 120 can sense the neonate's physiological parameter while the clamp 120 occludes blood flow in the cord.

The present disclosure has been described in terms of one or more non-limiting examples and embodiments, and it should be appreciated that many equivalents, alternatives, variations, and modifications, aside from those expressly stated, are possible and within the scope of the disclosure.

What is claimed is:

1. A neonate physiological monitoring system comprising:
   an umbilical cord clamp comprising:
      a sensor;
      a first clamping arm having first and second notches;
      a second clamping arm having first and second protrusions, and wherein the second clamping arm is configured to moveably engage the first clamping arm; and
      one or more deformable legs resiliently coupling the sensor to one of the first or second clamping arms; and
   wherein the umbilical cord clamp is moveable between an open position and first and second clamped positions in which the first clamping arm and the second clamping arm are mechanically coupled and the sensor contacts the umbilical cord to sense a physiological parameter of a neonate;
   wherein the first protrusion engages the second notch in the first clamped position to provide a first pressure to the umbilical cord;
   wherein the first protrusion engages the first notch and the second protrusion engages the second notch in the second clamped position to provide a second pressure to the umbilical cord that is greater than the first pressure;
   wherein the one or more deformable legs are compressed in the second clamped position; and
   a base station operable with the umbilical cord clamp, the base station configured to:
      (i) generate an interrogation signal for wireless transmission to the sensor of the umbilical cord clamp, and
      ii) in response to the wireless transmission of the interrogation signal, receive a response signal that is indicative of the sensed physiological parameter of the neonate.

2. The neonate physiological monitoring system of claim 1, wherein the base station includes at least one controller configured to process the response signal to determine information regarding the physiological parameter of the neonate based upon the signal indicative of the sensed physiological parameter.

3. The neonate physiological monitoring system of claim 2, wherein the determined information regarding the physiological parameter of the neonate is at least one of (i) heart rate (ii) heart beat strength, or (iii) a heart rate trend.

4. The neonate physiological monitoring system of claim 1, wherein the sensor includes a transducer configured such that an electrical property of the transducer changes to sense the physiological parameter of the neonate.

5. The neonate physiological monitoring system of claim 1, wherein the physiological parameter sensed by the sensor is a physical pulsation of the umbilical cord.

6. The neonate physiological monitoring system of claim 1, wherein the sensor includes (i) at least one resonance frequency antenna having a resonance frequency, and (ii) a measurement transducer that changes the resonance frequency of the at least one resonance frequency antenna upon said sensing of the physiological parameter of the neonate.

7. The neonate physiological monitoring system of claim 6, wherein the sensor includes at least one power receiving antenna that receives power wirelessly from the base station.

8. The neonate physiological monitoring system of claim 6, wherein the sensor includes at least one identifier circuit configured to, in response to a signal generated by the base station, provide at least one of (i) calibration instructions, (ii) neonate data, or (iii) alarm or response thresholds.

9. The neonate physiological monitoring system of claim 6, wherein the sensor includes a reference transducer configured to sense noise or interference signals, and wherein the base station is configured to control the sensed noise from the sensed physiological parameter of the neonate by comparing the sensed physiological parameter of the neonate to the sensed noise or interference signals.

10. The neonate physiological monitoring system of claim 1, wherein the base station is configured to process the response signal indicative of the sensed physiological parameter of the neonate using a Goertzel algorithm that isolates the physiological parameter of the neonate.

11. The neonate physiological monitoring system of claim 1, wherein the base station includes a bed sized and structured for supporting the neonate and a transducer configured to transmit the interrogation signal or receive the response signal.

12. The neonate physiological monitoring system of claim 1, wherein the sensor is resiliently coupled to the second clamping arm such that the sensor moves between (i) a first sensor position with respect to the second clamping arm in the first clamped position, and (ii) a second, different sensor position with respect to the second clamping arm in the second clamped position.

13. The neonate physiological monitoring system of claim 1, wherein the sensor includes (i) at least one resonance frequency antenna having a resonance frequency, and (ii) a measurement transducer that changes the resonance frequency of the at least one resonance frequency antenna upon said sensing of the physiological parameter of the neonate.

14. The neonate physiological monitoring system of claim 1, wherein the sensor is resiliently coupled to the second clamping arm such that the sensor is positioned closer to the clamping arm in the second clamped position than in the first clamped position.

15. A neonate physiological monitoring method comprising:

sensing a physiological parameter of a neonate via a sensor coupled to an umbilical cord of the neonate, wherein the sensor is coupled to a clamp having a first mechanically predefined clamped position in which a protrusion of the clamp engages a notch of the clamp and a second mechanically predefined clamped position in which two protrusions of the clamp respectively engage two notches of the clamp, wherein the clamp is moveable between an open position, the first mechanically predefined clamped position in which the clamp does not occlude blood flow and the sensor senses the physiological parameter, and the second mechanically predefined clamped position in which the clamp occludes blood flow and the sensor senses the physiological parameter;

transmitting an interrogation signal wirelessly to the sensor; and in response to transmitting the interrogation signal, receiving a response signal wirelessly that is indicative of the sensed physiological parameter of the neonate.

16. The neonate physiological monitoring method of claim 15, wherein (i) the sensor, when clamped to the umbilical cord of the neonate in the first clamping position, senses the physiological parameter of the neonate and the umbilical cord is not occluded, and (ii) the sensor, when clamped to the umbilical cord of the neonate in the second clamping position, senses the physiological parameter of the neonate and the umbilical cord is occluded.

17. The neonate physiological monitoring method of claim 15, wherein said sensing includes changing a resonant frequency of at least one antenna of the sensor.

18. The neonate physiological monitoring method of claim 15, which includes removing noise or interference from said sensing of the physiological parameter of the neonate.

19. The neonate physiological monitoring method of claim 15, wherein said sensing of the physiological parameter of the neonate includes at least one of (i) sensing an intermittent signal, or (ii) sensing a non-peripheral pulse.

20. An umbilical cord clamp comprising:
a first clamping arm;
a second clamping arm;
a sensor coupled to the second clamping arm; and
one or more deformable legs resiliently coupling the sensor to the second clamping arm;
wherein the first clamping arm is moveable relative to the second clamping arm between (i) a first clamped position in which the sensor contacts the umbilical cord to sense a physiological parameter of a neonate and the clamp does not occlude blood flow in the umbilical cord, and (ii) a second, different clamped position in which the sensor contacts the umbilical cord to sense the physiological parameter of the neonate and the clamp occludes blood flow in the umbilical cord;
wherein (i) the first clamping arm defines first and second notches, (ii) the second clamping arm includes first and second protrusions, (iii) the first protrusion is positioned in the second notch in the first clamped position, and (iv) the first and second protrusions are positioned in the first and second notches, respectively, in the second clamped position; and
wherein the one or more deformable legs are compressed in the second clamped position.

21. The umbilical cord clamp of claim 20, wherein the sensor is moveably coupled to the second clamping arm such that the sensor moves between (i) a first sensor position in the first clamped position, and (ii) a second, different sensor position in the second clamped position.

22. The umbilical cord clamp of claim 20, wherein the sensor is resiliently coupled to the second clamping arm such that the sensor moves between (i) a first sensor position in the first clamped position, and (ii) a second, different sensor position in the second clamped position.

23. The umbilical cord clamp of claim 20, wherein the sensor includes (i) at least one resonance frequency antenna having a resonance frequency, and (ii) a measurement transducer that changes the resonance frequency of the at least one resonance frequency antenna upon said sensing of the physiological parameter of the neonate.

24. The umbilical cord clamp of claim 23, wherein the sensor includes at least one power receiving antenna that receives power wirelessly.

25. The umbilical cord clamp of claim 23, wherein the sensor includes a reference transducer configured to sense noise or interference signals, and communicate said sensing of the physiological parameter of the neonate to a remote processor that is configured to use the sensed noise or interference signals to cancel the noise or interference signals from the sensed physiological parameter of the neonate.

26. The umbilical cord clamp of claim 20, wherein (i) the first clamping arm defining first and second notches includes a lip extending from an end portion the first clamping arm, the first and second notches defined in the lip, and (ii) and the first and second protrusions of the second clamping arm are positioned on an end face of the second clamping arm.

27. The umbilical cord clamp of claim 20, wherein the first protrusion includes a ramp to allow the first notch to slide over the ramp to clamp the first and second clamping arms in the first clamped position, and the second protrusion includes a ramp to allow the second notch to slide over the ramp to clamp the first and second clamping arms in the second clamped position.

28. The umbilical cord clamp of claim 20, wherein the first clamping arm is moveable relative to the second clamping arm via one of a (i) pivot mechanism or (ii) a hinge mechanism.

29. The umbilical cord clamp of claim 20, wherein the first clamping arm includes first teeth positioned on a first inner engaging surface of the first clamping arm, and the second clamping arm includes second teeth positioned on an opposing inner engaging surface of the second clamping arm, the first and second teeth aiding in securing the first and second clamping arms, respectively, to the umbilical cord when the first and second clamping arms are in the first and second clamped positions.

* * * * *